United States Patent [19]

Kasprzak

[11] Patent Number: 5,302,382

[45] Date of Patent: Apr. 12, 1994

[54] SILICONE CONTAINING PERSONAL CARE PRODUCTS

[75] Inventor: Kenneth A. Kasprzak, Saginaw, Mich.

[73] Assignee: Dow Corning Corporation, Midland, Mich.

[21] Appl. No.: 71,730

[22] Filed: Jun. 3, 1993

[51] Int. Cl.⁵ ............................................. A61K 31/765
[52] U.S. Cl. ................................. 424/78.03; 424/401; 514/844; 514/847; 514/937
[58] Field of Search .............................. 424/401, 78.03; 514/844, 846, 847, 937

[56] References Cited

U.S. PATENT DOCUMENTS 5,118,507  6/1992  Clement ............................... 424/401

Primary Examiner—Thurman K. Page
Assistant Examiner—Jyothsna Venkat
Attorney, Agent, or Firm—Jim L. DeCesare

[57] ABSTRACT

A method of making a stable emulsified personal care product by (i) forming an anhydrous silicone mixture which includes a silicone such as a silicone oil or a silicone gum, the mixture further including a first silicone oxyalkylene copolymer, and a second silicone oxyalkylene copolymer; (ii) forming an aqueous based pre-emulsified personal care product; and (iii) adding the anhydrous silicone mixture directly to the pre-emulsified personal care product without further emulsification.

11 Claims, No Drawings

SILICONE CONTAINING PERSONAL CARE PRODUCTS

BACKGROUND OF THE INVENTION

This invention is directed to personal care products for application to the skin which contain certain silicone skin conditioning agents in combination with certain silicone surfactants. When blended together in accordance with the teaching of the present invention, the silicone skin conditioning agents and the silicone surfactants can be added directly to aqueous based pre-emulsified personal care products without further emulsification.

The use of silicones in personal care products for the skin has been increasing dramatically since about 1976. Because of their unique properties, silicones have become a major ingredient in a number of personal care products. This growth can be attributed to several factors, among which are (i) their ability in providing excellent emolliency and lubricity which softens and moisturizes the skin; (ii) their provision of water repellency; and (iii) their capability in allowing the formation of thin films on the skin in order that no greasy or sticky feeling is imparted to the skin from the personal care product.

However, one of the principal hindrances to the use of silicones is their limited solubility in water and other polar media. This has been viewed as a problem by some formulators who require higher solubility. One solution has been to produce an emulsion of water and the silicone. This solution, however, has certain disadvantages in that an emulsifier with the proper solubility has to be found, the oil and water phases of the emulsion have to be prepared in separate containers, and then the two phases must be combined under high shear using Eppenbach mixers or colloid mills. This emulsion procedure entails what has been viewed by some to be unnecessary added time and expense, which ideally could be avoided.

The present invention seeks to provide a more simplified approach to the problem, and in which emulsification of the silicone prior to its addition into the personal care product is not required, and yet in which stable personal care products can be obtained.

SUMMARY OF THE INVENTION

The invention relates to an anhydrous silicone mixture containing certain silicone oxyalkylene copolymers, certain skin conditioning agents including silicone oils which are volatile and silicone oils which are nonvolatile, silicone gums, or mixtures of silicone oils and gums.

What is unexpected about the present invention is that the anhydrous silicone mixture can be added directly to an aqueous based pre-emulsified personal care product without further emulsification. The personal care product containing the anhydrous silicone mixture has been found to possess good stability in terms of shelf life and freeze/thaw characteristics.

The uniqueness of the present invention will become more apparent from a consideration of the following detailed description thereof.

DETAILED DESCRIPTION OF THE INVENTION

The anhydrous silicone mixture prepared in accordance with the present invention typically contains (i) a silicone fluid such as a volatile cyclic silicone or a volatile short chain linear silicone, a linear non-volatile silicone fluid, an ultra high viscosity silicone gum, or mixtures of silicone fluids and gums; (ii) an ethylene oxide/propylene oxide silicone copolymer which will be referred to hereinafter as an "EO/PO Silicone Surfactant"; and (iii) an ethylene oxide silicone copolymer which will be referred to hereinafter as an "EO Silicone Surfactant".

The "EO/PO Silicone Surfactant" is a siloxane polyether having the formula:

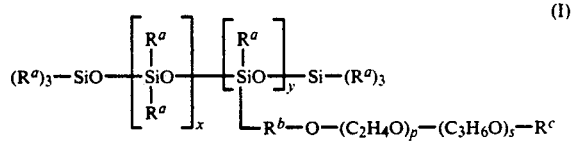

(I)

wherein $R^a$ is an alkyl group of one to six carbon atoms; $R^b$ is the radical $-C_mH_{2m}-$; $R^c$ is a terminating radical which can be hydrogen, an alkyl group of one to six carbon atoms, or an aryl group such as phenyl; m has a value of two to eight; p and s have values such that the oxyalkylene segment $-(C_2H_4O)_p-(C_3H_6O)_s-$ has a molecular weight in the range of 400 to 5,000; the segment preferably having fifty to one hundred mole percent of oxyethylene units $-(C_2H_4O)_p-$ and one to fifty mole percent of oxypropylene units $-(C_3H_6O)_s-$; x has a value of 80 to 120; and y has a value of 2 to 10.

Preferably $R^a$ and the terminating radical $R^c$ are methyl groups; m is preferably three or four whereby the group $R^b$ is most preferably the radical $-(CH_2)_3-$; and the values of p and s are such as to provide a molecular weight of the oxyalkylene segment $-(C_2H_4O)_p-(C_3H_6O)_s-$ of between about 1,000 to 3,000. Most preferably p and s should each have a value of about 18 to 28.

The "EO Silicone Surfactant" is a siloxane polyether having the formula:

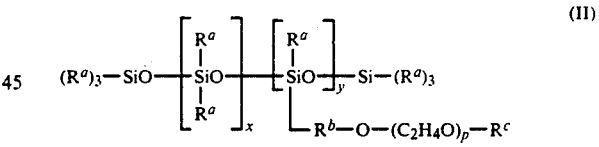

(II)

wherein $R^a$ is an alkyl group of one to six carbon atoms; $R^b$ is the radical $-C_mH_{2m}-$; $R^c$ is a terminating radical which can be hydrogen, an alkyl group of one to six carbon atoms, or an aryl group such as phenyl; m has a value of two to eight; p has a value of 8 to 16; x has a value of 6 to 12; and y has a value of 1 to 8.

It should be understood that in both Formulas (I) and (II) shown above, that the siloxane-oxyalkylene copolymers of the present invention may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^a$ substituents which are attached to the two terminal silicon atoms at the end of the siloxane chain can be substituted with the segment $-R^b-O-(C_2H_4O)_p-(C_3H_6O)_s-R^c$ or with the segment $-R^b-O-(C_2H_4O)_p-R^c$. In some instances, it may be desirable to provide the segment $-R^b-O-(C_2H_4O)-$ $_p$—(C$_3$H$_6$O)$_s$—R$^c$ or the segment —R$^b$—O—(C$_2$H$_4$O)$_p$—R$^c$ at locations which are in the siloxane chain as well as at locations at one or both of the siloxane chain ends.

Methods of making such siloxane-oxyalkylene copolymers are known in the art, and are described in detail for example, in the standard volume entitled "Chemistry and Technology of Silicones", Walter Noll, Academic Press Inc., 1968, Pages 373-376.

For the sake of brevity, the siloxane polyether of Formula (I) shall be referred to in the examples as the "EO/PO Silicone Surfactant A"; and the siloxane polyether of Formula (II) shall be referred to as the "EO Silicone Surfactant". It should be understood that where reference is made to "EO/PO Silicone Surfactant A" in the examples, that this particular material constitutes a mixture containing about thirteen percent by weight of the EO/PO silicone surfactant as active ingredient, and about eighty-seven percent by weight of a volatile cyclic silicone. Where reference is made to an "EO/PO Silicone Surfactant B", the "B" material is essentially the same as "EO/PO Silicone Surfactant A", except that material "B" does not contain the volatile cyclic silicone.

The HLB value of "EO/PO Silicone Surfactant A" is about 1.8. The HLB value of the "EO Silicone Surfactant" is about 13.2. The value of the "EO/PO Silicone Surfactant B" is about 5.9.

The volatile silicone used in the "EO/PO Silicone Surfactant A", and the volatile silicone which may be used as a component of the anhydrous silicone mixture is a low viscosity methylsilicone fluid. These volatile low viscosity methylsilicone fluids correspond to the formula (CH$_3$)$_a$SiO$_{(4-a/2)}$ wherein a is an integer having an average value of from two to three. The methylsilicone fluid contains siloxane units joined by Si—O—Si bonds. Representative units are (CH$_3$)$_3$SiO$_{178}$, (CH$_3$)$_2$SiO$_{2/2}$, (CH$_3$)SiO$_{3/2}$, and SiO$_{4/2}$. These units are present in molar amounts such that there is provided an average of from about two to three methyl groups per silicon atom in the methylsilicone fluid; whereby the methylsilicone fluid has a viscosity of less than about one hundred centistokes measured at twenty-five degrees Centigrade, preferably less than about five centistokes.

The volatile low viscosity methylsilicone fluid contains dimethylsiloxane units and optionally trimethylsiloxane units. Representative compounds are cyclopolysiloxanes of the formula [(CH$_3$)$_2$SiO]$_x$, and linear short chain siloxane compounds of the formula (CH$_3$)$_3$SiO[(CH$_3$)$_2$SiO]$_y$Si(CH$_3$)$_3$, in which x is an integer having a value of from three to ten, and y is an integer having a value of from zero to about four.

The volatile low viscosity methylsilicones have boiling points generally less than about two hundred-fifty degrees Centigrade, and as noted above, preferably possess viscosities less than about ten centistokes. Most preferably, the viscosity is between 0.65 to 5.0 centistokes.

The cyclopolysiloxanes have been assigned the adopted name "CYCLOMETHICONE" by the Cosmetics, Toiletries and Fragrance Association, Inc., Washington, D.C. (CTFA). Both the cyclopolysiloxanes and the volatile linear siloxanes are clear fluids which are essentially odorless, nontoxic, nongreasy and nonstinging. Cosmetically, these methylsilicone fluids are nonirritating to the skin and exhibit enhanced spreadability and ease of rub-out when applied to the skin. Once applied to the skin, the materials evaporate leaving behind no residue.

Methylsilicone fluids which are operable in accordance with the present invention leave substantially no residue after thirty minutes at room temperature when one gram of the fluid is placed at the center of a No. 1 circular filter paper having a diameter of 185 mm supported at its perimeter in open room atmosphere.

By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical.

Representative methylsilicone fluids found to be especially useful in accordance with the present invention are hexamethyldisiloxane which has a boiling point of 99.5 degrees Centigrade and the formula Me$_3$SiOSiMe$_3$; octamethyltrisiloxane which has a boiling point of 152 degrees Centigrade and the formula Me$_3$SiOMe$_2$SiOSiMe$_3$; hexamethylcyclotrisiloxane which has a boiling point of 133 degrees Centrigrade and the formula [(Me$_2$)SiO]$_3$; octamethylcyclotetrasiloxane which has a boiling point of 171 degrees Centigrade and the formula [(Me$_2$)SiO]$_4$; and decamethylcyclopentasiloxane which has a boiling point of 205 degrees Centigrade and the formula [(Me$_2$)SiO]$_5$.

These methysilicone fluids may be used alone, or as mixtures in combinations of two or more. Mixtures of the methylsilicone fluids will result in a volatile material having an evaporating behavior different from any one of the individual methylsilicone fluids.

In some instances, it may be desirable to replace one or more of the methyl groups in the methylsilicone fluid with other groups. Thus, there may be substituted alkyl radicals having two to twelve carbon atoms; or aryl radicals having six to ten carbon atoms.

The anhydrous silicone mixture may also contain a linear non-volatile silicone component which can be a polysiloxane film former having a viscosity in excess of five and up to 25,000,000 centistokes, preferably a within a range of about 5 to about 10,000 centistokes. A mixture of non-volatile polysiloxanes having relatively higher and relatively lower viscosities may also be employed. Such polysiloxanes contain the repeating unit

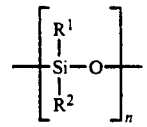

wherein n is an integer having a value greater than one; R$^1$ is an alkyl radical containing 1 to 40 carbon atoms, or a phenyl group; R$^2$ is an alkyl radical containing 1 to 7 carbon atoms, or a phenyl group. Illustrative polysiloxanes encompassed by the above formula are polydimethylsiloxane, polydiethylsiloxane, polymethylethylsiloxane, polymethylphenylsiloxane, polydiphenylsiloxanes, and copolymers of two or more of the foregoing siloxanes. Alkylmethylsilicone waxes such as polymethylstearylsiloxane may also be employed.

The anhydrous silicone mixture may additionally contain an ultra-high viscosity silicone gum. These silicone gums typically have the structure HOMe$_2$SiO(Me$_2$SiO)$_n$SiMe$_2$OH in which Me is methyl and n is an integer having a value of at least one and which can be as much as 10,000. These silicone gums are known in the art and detailed descriptions of such gums can be found, for example, in EP 0 460 683 A2 which is a European Patent Application published on Dec. 11, 1991. Another suitable type of ultra-high viscosity silicone gum which may be employed is a material of the formula Me$_3$SiO(Me$_2$SiO)$_n$SiMe$_3$ in which Me is methyl and n has a value of at least one and up to about 10,000.

Because of the high viscosity of the silicone gum, and for the purpose of facilitating its handling and processing, these materials are generally provided as blends with another volatile or non-volatile low viscosity silicone such as CYCLOMETHICONE, or a non-volatile linear silicone fluid having a viscosity of about 5 to 350 centistokes. Such dimethyl silicone polymers terminated with hydroxyl groups have been assigned the adopted name "DIMETHICONOL" by The Cosmetics, Toiletries and Fragrance Association, Inc., Washington, D.C. (CTFA). Blends of such silicone gums with a volatile low viscosity cyclic silicone have been assigned the adopted name "CYCLOMETHICONE (and) DIMETHICONOL" by the CTFA. Other blends of such silicone gums with a non-volatile low viscosity linear silicone have been assigned the adopted name "DIMETHICONE (and) DIMETHICONOL" by the CTFA. The DIMETHICONOL content of such blends is typically in the range of about 12 to 14 percent by weight, and the blend viscosity may range from 500 to about 20,000 centistokes, generally in the range of about 4,000 to 5,000 centistokes.

In some instances, it may be desirable to replace one or more of the hydroxy or methyl groups in the silicone gum with other substituents such as ethyl or vinyl, for example.

In addition, it may be desirable to include in the anhydrous silicone mixture other compatible materials such as waxes. Waxes which may be employed include carnauba, beeswax, ceresin, paraffin, candelilla, bayberry, montan, spermaceti, castor wax, ozokerite, microcrystalline waxes, alkylmethylsiloxane waxes, and Fisher-Tropsch waxes. Ester waxes may also be employed such as those products sold by Croda Surfactants, Ltd., North Humberside, England, under the tradename SYNCHROWAX AW1, BB, BE, BSE14, ERL, HGL, HR, HRS, RLS, and SE.

Emollient oils may also be included in the anhydrous silicone mixture, and among those oils which can be employed in the present invention include mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, butyl stearate, cetyl stearate, diisopropyl adipate, isodecyl oleate, diisopropyl sebacate, and lauryl lactate; fatty acids such as lauric, myristic, palmitic, stearic, oleic, linoleic, and behenic, acid; fatty alcohols such as lauryl, myristyl, cetyl, stearyl, isostearyl, oleyl, ricinoleyl, erucyl, and 2-octyl dodecanol, alcohols; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, N.J.; and hydrocarbons such as petrolatum and squalane.

The anhydrous silicone mixture of the present invention is prepared by simply mixing together the various silicone ingredients until a uniform blend is obtained. The anhydrous silicone mixture is then capable of being added directly to any aqueous based pre-emulsified personal care product, and without the necessity of any further emulsification in order to disperse the silicones in the personal care product. Preferably, the anhydrous silicone mixture contains 2-35 percent by weight of the "EO/PO Silicone Surfactant"; 0.1-10.0 percent by weight percent of the "EO Silicone Surfactant"; and 1-65 percent by weight of an ultra-high viscosity silicone gum; based on the total weight of the anhydrous silicone mixture.

The anhydrous silicone mixture is preferably added to the pre-emulsified personal care product in an amount of about 0.5 to about 10.0 percent by weight based on the weight of the personal care product. About one percent by weight of the anhydrous silicone mixture will generally be sufficient.

The invention is illustrated in more detail in the following examples.

EXAMPLE I

Into a container there was added and blended together 10.0 grams of the "EO/PO Silicone Surfactant A", and 2.0 grams of the "EO Silicone Surfactant". The "EO/PO Silicone Surfactant" contained 87 percent by weight of the ethylene oxide/propylene oxide silicone copolymer and 13 percent by weight of a volatile cyclic silicone. There was then added to the container 35.0 grams of a hydroxy terminated silicone gum which had been blended with 87.0 percent by weight of a linear non-volatile silicone fluid having a viscosity of about 5.0 centistokes measured at 25 degrees Centigrade. The two surfactants and the gum-blend were mixed together in the container until a uniform mixture was obtained. One gram of this anhydrous silicone mixture was added to 49.0 grams of a commercially available personal care skin cleansing product.

The personal care skin cleansing product selected was the OIL OF OLAY® Foaming Cleanser, a trademark and product of the Olay Company, Inc., Shelton, Conn. USA, a Procter & Gamble company. This aqueous based pre-emulsified foaming face wash composition contained water, potassium cocoyl hydrolyzed collagen, glycerin, sodium lauriminodiproprionate, sodium acrylate/steareth-20 methacrylate copolymer, sodium lauroyl sarcosinate, disodium cocoamphodiacetate, sodium lauryl sulfate, hexylene glycol, Polyquaternium-10, a fragrance, phenoxyethanol, DMDM hydantoin, tetrasodium EDTA, mica, and titanium dioxide. It should be understood, however, that the present invention is applicable to other aqueous based pre-emulsified personal care products for general application to the skin.

EXAMPLE II

The personal care skin cleansing product prepared in accordance with the teaching in Example I was tested by a group of at least two and as many as four sensory panel trained individuals. One-half gram of the product was applied to a small pre-dampened facial sponge, and the test material was applied to the volar forearm in a small circular motion of about two circular strokes per second. Fifty light strokes were used by the volunteers to apply the product.

A rinse was used by the volunteers with forty degree Centigrade tap water, and the rinse was carried out by placing the arm under tap water for fifteen seconds. The arm was pat dried with a paper towel and allowed to completely dry for 2–5 minutes. Evaluations were made by the volunteers by lightly rubbing the treated area and comparing to a "control" area, which had been treated with unaltered OIL OF OLAY® Foaming Cleanser. The volunteers were asked to determine if the treatments were significantly different from one another. The volunteers almost without exception indicated that a smoother, silkier feel, was deposited on the skin with the silicone containing product than with the unaltered OIL OF OLAY® Foaming Cleanser, and that the silicone containing product looked good from the standpoint of uniformity.

EXAMPLE III

The personal care skin cleansing product prepared in Example I was tested for its shelf life by subjecting the product to a freeze-thaw cycling from +20 to −20 degrees Centigrade. Five complete cycles were completed. The product was evaluated as stable at the end of five days.

EXAMPLE IV

Examples I–III were repeated except that to the container in Example I there was added 35.0 grams of a hydroxy terminated silicone gum blended with 60.0 percent of a linear non-volatile silicone fluid having a viscosity of about 350 centistokes measured at 25 degrees Centigrade. The results reported were identical to the results obtained in Examples I–III.

Other variations and modifications may be made in the compounds, compositions, and methods described herein without departing from the essential features and concepts of the present invention. The forms of the invention described herein are exemplary only and are not intended as limitations on the scope of the invention which is defined in the appended claims.

What which is claimed is:

1. A method of making a stable emulsified personal care product having as an ingredient thereof a silicone skin conditioning agent, comprising (i) forming an anhydrous silicone mixture which includes a silicone selected from the group consisting of volatile cyclopolysiloxanes having the formula in which x has a value of 3 to 10, non-volatile linear polysiloxanes having a viscosity of 5 to 10,000 centistokes, and a silicone gum, the mixture further including a first silicone oxyalkylene copolymer, and a second silicone oxyalkylene copolymer; (ii) forming a pre-emulsified aqueous based personal care product; and (iii) adding the anhydrous silicone mixture directly to the pre-emulsified personal care product without further emulsification, the first silicone oxyalkylene copolymer in the anhydrous silicone mixture being a siloxane polyether of the formula:

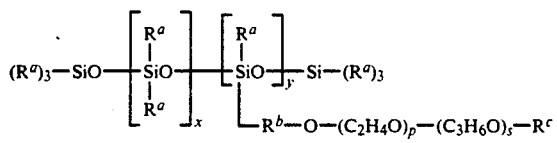

wherein $R^a$ is an alkyl group of one to six carbon atoms; $R^b$ is the radical $-C_mH_{2m}-$; $R^c$ is a terminating radical selected from the group consisting of hydrogen, an alkyl group of one to six carbon atoms, and an aryl group; m has a value of two to eight; p and s each have values between 18 to 28; x has a value of 80 to 120; and y has a value of 2 to 10.

2. A method according to claim 1 in which $R^a$ and the terminating radical $R^c$ are methyl groups; and m is three or four.

3. A method according to claim 1 in which the second silicone oxyalkylene copolymer in the anhydrous silicone mixture is a siloxane polyether of the formula:

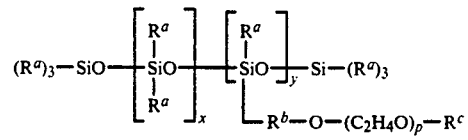

wherein $R^a$ is an alkyl group of one to six carbon atoms; $R^b$ is the radical $-C_mH_{2m}-$; $R^c$ is a terminating radical selected from the group consisting of hydrogen, an alkyl group of one to six carbon atoms, or an aryl group; m has a value of two to eight; p has a value of 8 to 16; x has a value of 6 to 12; and y has a value of 1 to 8.

4. A method according to claim 3 in which the silicone in the anhydrous silicone mixture is the silicone gum of the structure $HOMe_2SiO-(Me_2SiO)_nSiMe_2OH$ in which Me is methyl and n is an integer having a value of from one to 10,000.

5. A method according to claim 4 in which the silicone gum is blended with a non-volatile linear silicone fluid having a viscosity of 5 to 350 centistokes.

6. A method according to claim 3 in which the silicone in the anhydrous silicone mixture is the silicone gum of the structure $Me_3SiO(Me_2SiO)_nSiMe_3$ in which Me is methyl and n is an integer having a value of from one to 10,000.

7. A stable emulsified personal care product prepared according to the method defined in claim 1.

8. A composition comprising an anhydrous silicone mixture which includes (i) a silicone selected from the group consisting of a silicone oil and a silicone gum, the mixture further including (ii) a first silicone oxyalkylene copolymer, and (iii) a second silicone oxyalkylene copolymer; the silicone (i) in the anhydrous mixture being a compound selected from the group consisting of volatile cyclopolysiloxanes having the formula $[(CH_3)_2SiO]_x$ in which x has a value of 3 to 10, and non-volatile linear polysiloxanes having a viscosity of 5 to 25,000,000 centistokes; the first silicone oxyalkylene copolymer (ii) in the anhydrous silicone mixture being a siloxane polyether of the formula:

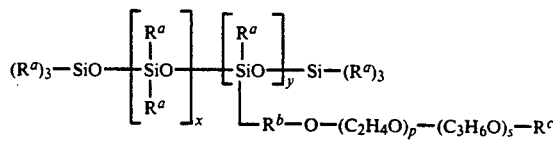

wherein $R^a$ is an alkyl group of one to six carbon atoms; $R^b$ is the radical $-C_mH_{2m}-$; $R^c$ is a terminating radical selected from the group consisting of hydrogen, an alkyl group of one to six carbon atoms, and an aryl group; m has a value of two to eight; p and s each have values between 18 to 28; x has a value of 80 to 120; and y has a value of 2 to 10; and in which the second silicone oxyalkylene copolymer (iii) in the anhydrous silicone mixture is a siloxane polyether of the formula:

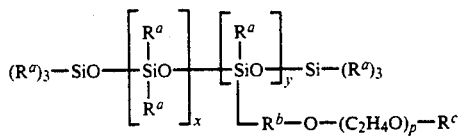

wherein $R^a$ is an alkyl group of one to six carbon atoms; $R^b$ is the radical $-C_mH_{2m}-$; $R^c$ is a terminating radical selected from the group consisting of hydrogen, an alkyl group of one to six carbon atoms, or an aryl group; m has a value of two to eight; p has a value of 8 to 16; x has a value of 6 to 12; and y has a value of 1 to 8.

9. A composition according to claim 8 in which the silicone in the anhydrous silicone mixture is the silicone gum of the structure $HOMe_2SiO\text{-}(Me_2SiO)_nSiMe_2OH$ in which Me is methyl and n is an integer having a value of from one to 10,000.

10. A composition according to claim 9 in which the silicone gum is blended with a non-volatile linear silicone fluid having a viscosity of 5 to 350 centistokes.

11. A composition according to claim 8 in which the silicone in the anhydrous silicone mixture is the silicone gum of the structure $Me_3SiO(Me_2SiO)_nSiMe_3$ in which Me is methyl and n is an integer having a value of from one to 10,000.

* * * * *